US00PP12838P2

(12) United States Plant Patent
Evison et al.

(10) Patent No.: US PP12,838 P2
(45) Date of Patent: Aug. 13, 2002

(54) CLEMATIS PLANT NAMED 'EVIRIN'

(76) Inventors: Raymond J. Evison, Domarie Vineries, Les Sauvagees, St. Sampsons, Guernsey GY2 4AF, C.I. (GB); Mogens N. Olesen, Poulsen Roser International, S.A.R.L., Broze, F-81600 Gaillac (FR)

( * ) Notice: Subject to any disclaimer, the term of this patent is extended or adjusted under 35 U.S.C. 154(b) by 0 days.

(21) Appl. No.: 09/177,981

(22) Filed: Oct. 22, 1998

(51) Int. Cl.[7] ..... A01H 5/00
(52) U.S. Cl. ..... Plt./228

(58) Field of Search ..... Plt./228, 226

*Primary Examiner*—Howard J. Locker
*Assistant Examiner*—Michelle Kizilkaya

(57) ABSTRACT

A new compact clematis cultivar which displays single pale white flowers with pale violet margins. The cultivar is free flowering. The variety successfully propagates from soft-wood cuttings and traditional methods and is suitable for ornamental use in outdoor settings in a variety of climatic conditions. This new and distinct variety has shown to be uniform and stable in the resulting generations from asexual propagation.

1 Drawing Sheet

SUMMARY OF THE INVENTION

The present invention constitutes a new and distinct variety of clematis. The variety was discovered as a chance seedling of unknown parentage in a cultivated area. The variety is a member of the clematis patens group. The new variety is named 'EVIrin'.

The following unique combination of characteristics that are outstanding in 'EVIrin' have been repeatedly observed in asexually propagated progeny and distinguish the variety from all other varieties of which we are aware:

1. Pale white to pale violet flowers with contrasting dark red centers,

2. Strongly undulated tepal margins,

4. Excellent flower production on compact flowering stems, and

5. Compact growth suitable for growing in containers.

These qualities required improvement in clematis varieties that were in commercial cultivation and have been substantially achieved in the new variety, as evidenced by the unique combination of characteristics that are present in 'EVIrin' which distinguish it from all other varieties of which we are aware.

'EVIrin' was selected by the inventors as a single plant from the progeny of the chance hybridization in their clematis development program in Domarie Vineries Les Sauvagees, St. Sampsons, Guernsey, Channel Islands, United Kingdom in 1990.

Asexual reproduction of 'EVIrin' by cuttings was first done by Raymond J. Evison and Mogens N. Olesen in Domarie Vineries Les Sauvagees, St. Sampsons, Guernsey, Channel Islands, United Kingdom in Summer, 1990. This initial and subsequent propagations have demonstrated that the characteristics of 'EVIrin' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers and leaves of the new variety, with different flowers shown in various stages of maturity. Specifically illustrated in SHEET 1:

1. Flower buds,
2. Half opened flower,
3. Recently opened flower bloom;
4. Mature flower bloom,
5. Open flower, reverse view of tepals,
6. Individual tepals, upper and reverse side view,
7. Foliage, leaf, and stem.

DETAILED DESCRIPTION OF THE VARIETY

The following is a detailed description of 'EVIrin', as observed in its growth throughout the flowering period in glasshouses at Domarie Vineries Les Sauvagees, St. Sampsons, Guernsey, Channel Islands, United Kingdom and in a field nursery in Jackson County, Ore. At these locations, the variety, a vine, exhibits a combination of woody and herbaceous growth. Certain phenotypical characteristics of the variety may vary under different environmental, cultural, agronomic, seasonal, and climatic conditions. Color references are made using The Royal Horticultural Society (London, England) Colour Chart, 1995; except where common terms of color are used.

For a comparison, the nearest existing clematis variety is 'SNOW QUEEN'. Chart 1 details several physical characterstics of 'EVIrin' and 'Snow Queen', and unpatented Clematis variety.

Chart 1

| | 'EVIRIN' | 'SNOW QUEEN' |
|---|---|---|
| Tepal Margins | Medium-strong undulation | Weak undulation |
| Tepal Main Color | Violet Group 84D | Near white RHS 159D |
| Anthers | Dark red | Medium red |

-continued

Chart 1

| | 'EVIRIN' | 'SNOW QUEEN' |
|---|---|---|
| Number of Flowers | Abundant number of flowers | Average number of flowers |

Seed parent: Unknown.
Pollen parent: Unknown.
Classification:
*Botanical.*—*Clematis L.*

FLOWER AND FLOWER BUD

Blooming habit: In Jackson County, Oreg. the variety first blooms in late May through June and blooms again September through the first frost in October.
Flower bud:
*Size.*—40–50 mm in length.
*Bud form.*—Elliptic and ovoid.
*Bud color.*—Green Group 143C at ¼ opening.
*Tepals.*—Violet Group 84D.
*Peduncle.*—Surface: Smooth. Length: 80–100 mm average length. Color: Yellow-Green Group 144C. Strength: Semi-erect.
*Borne.*—Singly.
Flower bloom:
*Size.*—Medium. 160 mm on average. Upon opening, convex.
*Form.*—Convex. Completely open flat.
*Color.*—Upon opening, the marginal zone of the upper surface of the tepal is Purple Group 76A. Upon opening, the upper surface has a central bar of White Group 155C to Violet Group 84D. Upon opening, the marginal zone of the reverse surface of the tepal is Purple Group 76A. The central bar is Yellow-Green 145D to Green-White 157A. After opening, the marginal zone of the upper surface of the tepal is Violet Group 84D. After opening, the central bar is White Group 155C. After opening, the marginal zone of the reverse surface of the tepal is Violet Group 84D. After opening, The central bar is Green-White Group 157A. The bases of the tepals are Green-White Group 157A to Yellow-Green Group 145C.
*Fragrance.*—None.
*Lasting quality on plant and as a cut flower.*—On the plant the flowers last 7 to 10 days. As a cut flower, the flowers last 6 to 8 days.
*Tepal count.*—Single. Average range: 6–8 per bloom.
*Shape.*—Individual tepal shape is elliptic.
*Cross section.*—Flat.
*Undulation of margin.*—Medium-strong.
*Tepal apex.*—Narrowly acute.
*Recurvature of tip.*—Slightly curved.
*Persistence.*—Tepals drop off cleanly.
*Arrangement.*—Tepals are arranged evenly around the axis of the flower.
Reproductive organs:
*Pollen.*—Color: Grey-Black Group 202D. Abundance: Average.
*Anthers.*—Size: Medium to large. Color: Greyed-Purple Group 187A to Purple Group 77A.
*Filaments.*—Color: White Group 155C to Green-White Group 157C.
*Stigmas.*—Color: White Group 155C.
*Styles.*—Color: Green-White Group 157C.
*Ovaries.*—Normal position.
*Seed production.*—Variety produces viable seed.

PLANT

Plant form: Climbing and spreading.
Plant growth: Average vigor.
Height: Plant requires support by trellising to obtain maximum vertical growth. An established, supported plant grows 2.0 to 2.5 meters in height each growing season in Oregon.
Hardiness: Trials to date show the variety hardy in USDA Zones 4–9.
Stems:
*Color.*—Young wood: Greyed-Purple Group 183D. Older wood: Brown Group 200D.
*Internodes.*—Shape: Cylindrical. Length: 100–150 mm.
*Petioles and Petiolules.*—Average length: Petioles=40–50 mm Petiolule=5–15 mm Petiole color: Greyed-Purple Group 183D. Petiolule color: Yellow-Green Group 144C. Clasping: Clasps by winding leaf petioles
*Bark.*—Young wood: Smooth. Older wood: Smooth.
Plant foliage: Deciduous. Trifoliate. Veins are parallel to the margin of the leaf.
*Compound leaf and individual leaflet size.*—The compound leaves have an average overall length of 250–300 mm and width of 150 mm. The individual leaflets measure 80 mm long and 50–60 mm wide.
*Abundance.*—Average.
*Color.*—Upper surface: Medium green. Green Group 137B. Veins are Green Group 137C. Lower surface: Medium green. Green Group 137C. Juvenile foliage: Internodes: Yellow-Green Group 144C with intonations of Greyed-Red Group 180C. Foliage: Yellow-Green Group 144C. Mature foliage: Internodes: Greyed-Purple Group 183D. Foliage: Green Group 137A.
Plant leaves and leaflets:
*Stipules.*—Absent.
*Petiole.*—Length: 40–50 mm. Underneath: Smooth.
*Leaf edge.*—Terminal leaflet margin is entire.
*Shape.*—Base of leaflet: Rounded. Apex of leaflet: Acute.
*Texture.*—Medium textured. Upper side: Glabrous. Lower side: Ribbed.
*Surface.*—Matte Finish.
*Leaf arrangement.*—Opposite.
Disease resistance: Average disease resistance to mildew and Botrytis.

We claim:

1. A new and distinct variety of clematis plant, substantially as herein illustrated and described as a distinct and novel clematis variety due to its abundant white flowers with pale violet margins, good keepability, suitability for production from softwood cuttings, and compact growth which make the variety suitable for distribution in the floral and nursery industry.

* * * * *

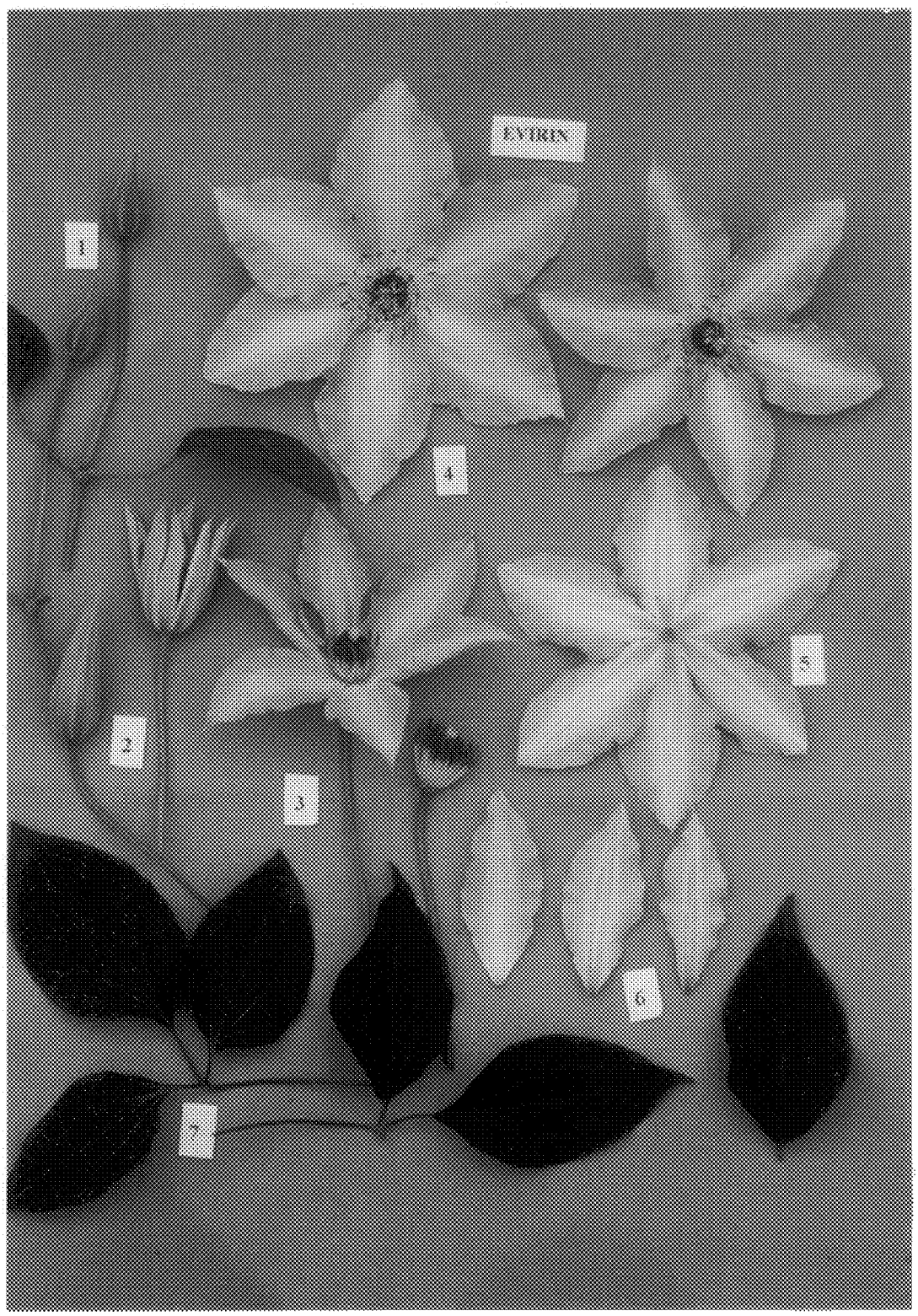
LYRIN
1
2
3
4
5
6
7